United States Patent [19]

Dowle et al.

[11] Patent Number: 4,833,153
[45] Date of Patent: May 23, 1989

[54] INDOLE DERIVATIVES

[75] Inventors: Michael D. Dowle, Ware; Brian Evans, Buntingford, both of England; Peter Clark, Edmonton, Canada

[73] Assignee: Glaxo Group Limited, London, England

[21] Appl. No.: 928,037

[22] Filed: Nov. 7, 1986

[30] Foreign Application Priority Data

Nov. 8, 1985 [GB] United Kingdom ............... 8527619
Nov. 8, 1985 [GB] United Kingdom ............... 8527620

[51] Int. Cl.[4] ................ A61K 31/40; C07D 233/06
[52] U.S. Cl. .................................. 514/415; 514/414; 514/256; 514/402; 548/348; 548/504; 544/333
[58] Field of Search ............... 544/333; 548/336, 469, 548/503, 504, 505, 348; 514/256, 397, 415, 414, 402

[56] References Cited

U.S. PATENT DOCUMENTS

| | | | |
|---|---|---|---|
| 3,472,872 | 10/1969 | Bell | 548/469 |
| 3,663,610 | 5/1972 | Ecsery et al. | 562/435 |
| 3,673,188 | 6/1972 | Harsanyi et al. | 546/145 |
| 4,252,803 | 2/1981 | Webb | 514/415 |
| 4,636,521 | 1/1987 | Coates et al. | 514/414 |
| 4,650,810 | 3/1987 | Bays et al. | 514/414 |

Primary Examiner—Mary C. Lee
Assistant Examiner—Zinna Northington
Attorney, Agent, or Firm—Bacon & Thomas

[57] ABSTRACT

Compounds are disclosed of formula (I):

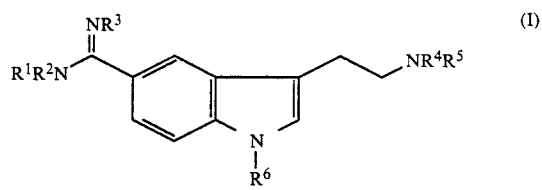

wherein one of $R^1$, $R^2$ and $R^3$ represents hydrogen, $C_{1-6}$ alkyl $C_{3-6}$ alkenyl, hydroxy, $C_{1-4}$ alkoxy or a $C_{2-5}$ alkoxycarbonyl group, a phenyl or substituted phenyl group or a phen($C_{1-4}$)alkyl or substituted phen($C_{1-4}$)alkyl group; and the other two each independently represents hydrogen, $C_{1-6}$ alkyl, or $R^2$ and $R^3$ together form an alkylene chain —$(CH_2)_n$—where n is 2 or 3, bridging the nitrogen atoms to which they are attached; $R^4$ and $R^5$, each independently represents hydrogen, $C_{1-3}$ alkyl or propenyl; $R^6$ represents hydrogen, $C_{1-3}$ alkyl, and the physiologically acceptable salts and solvates thereof.

The compounds (I) have potent and selective vasoconstrictor activity and are potentially useful for the treatment of migraine. The compounds (I) may be formulated in conventional manner as pharmaceutical compositions for administration by any convenient route.

9 Claims, No Drawings

INDOLE DERIVATIVES

This invention relates to indole derivatives, to processes for their preparation, to pharmaceutical compositions containing them and to their medical use, in particular to compounds and compositions of use in the treatment of migraine.

The pain of migraine is associated with excessive dilatation of the cranial vasculature, and known treatments for migraine include the administration of compounds having vasoconstrictor properties, such as ergotamine. However, ergotamine is a non-selective vasoconstrictor which constricts blood vessels throughout the body and has undesirable and potentially dangerous side effects. Migraine may also be treated by administering an analgesic, usually in combination with an antiemetic, but such treatments are of limited value.

There is thus a need for a safe and effective drug for the treatment of migraine, which can be used either prophylactically or to alleviate an established headache, and a compound having a selective vasoconstrictor activity would fulfil such a role.

We have now found a group of indole derivatives having potent and selective vasoconstrictor activity. The present invention thus provides an indole of the general formula (I)

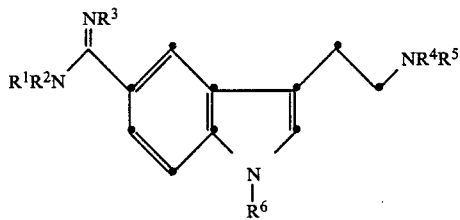

wherein one of $R^1$, $R^2$ and $R^3$ represents a hydrogen atom, a $C_{1-6}$ alkyl, $C_{3-6}$ alkenyl, hydroxy, $C_{1-4}$ alkoxy or a $C_{2-5}$ alkoxycarbonyl group, a phenyl or substituted phenyl group or a phen($C_{1-4}$)alkyl or substituted phen($C_{1-4}$)alkyl group; and the other two, which may be the same or different each represents a hydrogen atom or a $C_{1-6}$ alkyl group, or $R^2$ and $R^3$ together form an alkylene chain —$(CH_2)_n$— where n is 2 or 3, bridging the nitrogen atoms to which they are attached; $R^4$ and $R^5$, which may be the same or different each represents a hydrogen atom or a $C_{1-3}$ alkyl or propenyl group; $R^6$ represents a hydrogen atom or a $C_{1-3}$ alkyl group; and physiologically acceptable salts and solvates (e.g. hydrates) thereof.

It will be appreciated that compounds of the general formula (I) can exhibit tautomerism e.g. with respect to the amidine group and the invention includes within its scope all tautomeric forms of the compounds.

The invention also embraces all optical isomers of the compounds of formula (I), and their mixtures, including racemic mixtures.

Referring to the general formula (I), an alkyl group in $C_{1-6}$ alkyl, $C_{1-3}$ alkyl, phen($C_{1-4}$)alkyl, $C_{1-4}$ alkoxy and $C_{2-5}$ alkoxycarbonyl may be a straight or branched chain alkyl group, for example a methyl, ethyl or prop-2-yl group.

A $C_{3-6}$ alkenyl group may be for example a propenyl or butenyl group. It will be appreciated that the double bond in such alkenyl groups will not be adjacent to the nitrogen atom.

A phenyl or phen($C_{1-4}$)alkyl group in the compounds of formula (I) may be substituted for example by a $C_{1-4}$ alkyl, $C_{1-4}$ alkoxy or $C_{2-5}$ alkoxycarbonyl group, or a group of formula $R^7R^8NSO_2CH_2$— or $R^7R^8NCOCH_2$— where $R^7$ and $R^8$ each independently represents a hydrogen atom or a $C_{1-3}$ alkyl e.g. methyl group.

It will be appreciated that when $R^2$ and $R^3$ together represent a $C_2$- or $C_3$-alkylene chain the indole 5-substituent will be a dihydroimidazol-2-yl or a tetrahydropyrimidin-2-yl group.

A preferred class of compounds represented by the general formula (I) is that in which $R^1$ represents a $C_{1-3}$ alkyl group, for example a methyl group, and $R^2$ and $R^3$ each represents a hydrogen atom.

Another preferred class of compounds of formula (I) is that in which $R^1$ represents a substituted phenyl group and $R^2$ and $R^3$ each represents a hydrogen atom.

Yet another preferred class of compounds of formula (I) is that in which $R^2$ and $R^3$ together form a tetrahydropyrimidin-2-yl group.

A further preferred class of compounds of formula (I) is that in which $R^4$ and $R^5$ which may be the same or different each represents a hydrogen atom or a methyl or ethyl group such that the total number of carbon atoms in $R^4$ and $R^5$ together does not exceed two.

A particularly preferred compound according to the invention is 3-[2-(dimethylamino)ethyl]-N-ethyl-1H-indole-5-carboximidamide and the physiologically acceptable salts and solvates thereof.

Suitable physiologically acceptable salts of the indoles of general formula (I) include acid addition salts formed with inorganic or organic acids, for example hydrochlorides, hydrobromides, sulphates, nitrates, phosphates, tartrates, citrates, fumarates, maleates, succinates, and sulphonates e.g. mesylates. Other salts may be useful in the preparation of compounds of formula (I) e.g. creatinine sulphate adducts.

It will be appreciated that the invention extends to other physiologically acceptable equivalents of the compounds according to the invention, i.e. physiologically acceptable compounds which are converted in vivo into the parent compound of formula (I). Examples of such eqivalents include physiologically acceptable, metabolically labile N-acyl derivatives.

Compounds of the invention selectively constrict the carotid arterial bed of the anaesthetised dog, whilst having a negligible effect on blood pressure. Their selective vasoconstrictor action has also been demonstrated in vitro.

Compounds of the invention are useful in treating pain originating from dilation of the carotid vascular bed, in particular migraine and cluster headache.

Accordingly, the invention also provides a pharmaceutical composition adapted for use in human medicine which comprises at least one compound of formula (I) or a physiologically acceptable salt or solvate (e.g. hydrate) thereof and formulated for administration by any convenient route. Such compositions may be formulated in conventional manner using one or more pharmaceutically acceptable carriers or excipients.

Thus the compounds according to the invention may be formulated for oral, buccal, parenteral or rectal administration or in a form suitable for administration by inhalation or insufflation.

For oral administration, the pharmaceutical compositions may take the form of, for example, tablets or capsules prepared by conventional means with pharmaceutically acceptable excipients such as binding agents (e.g. pregelatinised maize starch, polyvinylpyrrolidone or hydroxypropyl methylcellulose); fillers (e.g. lactose, microcrystalline cellulose or calcium phosphate); lubricants (e.g. magnesium stearate, talc or silica); disintegrants (e.g. potato starch or sodium starch glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g. sorbitol syrup, methyl cellulose or hydrogenated edible fats); emulsifying agents (e.g. lecithin or acacia); non-aqueous vehicles (e.g. almond oil, oily esters or ethyl alcohol); and preservatives (e.g. methyl or propyl-p-hydroxybenzoates or sorbic acid).

For buccal administration the compositions may take the form of tablets or lozenges formulated in conventional manner.

The compounds of the invention may be formulated for parenteral administration by injection. Formulations for injection may be presented in unit dosage form e.g. in ampoules or in multi-dose containers, with an added preservative.

The compositions may take such forms as suspensions, solutions or emulsions in oily or aqueous vehicles, and may contain formulatory agents such as suspending, stabilising and/or dispersing agents. Alternatively, the active ingredient may be in powder form for constitution with a suitable vehicle, e.g. sterile pyrogen-free water, before use.

The compounds of the invention may also be formulated in rectal compositions such as suppositories or retention enemas, e.g. containing conventional suppository bases such as cocoa butter or other glycerides.

For administration by inhalation the compounds according to the invention are conveniently delivered in the form of an aerosol spray presentation from pressurized packs, with the use of a suitable propellant, e.g. dichlorodifluoromethane, trichlorofluoromethane, dichlorotetrafluoroethane, carbon dioxide or other suitable gas; or from a nebuliser. In the case of a pressurised aerosol the dosage unit may be determined by providing a valve to deliver a metered amount. Capsules and cartridges of e.g. gelatin for use in an inhaler or insufflator may be formulated containing a powder mix of a compound of the invention and a suitable powder base such as lactose or starch.

A proposed dose of the compounds of the invention for oral, parenteral, buccal or rectal administration to man for the treatment of migraine is 0.1 to 100 mg of the active ingredient per unit dose which could be administered, for example, up to 8 times per day, more usually 1 to 4 times per day.

It will be appreciated that it may be necessary to make routine variations to the dosage depending on the age and weight of the patient as well as the severity of the condition to be treated.

For oral administration a unit dose will preferably contain from 2 to 50 mg of the active ingredient. A unit dose for parenteral administration will preferably contain 0.2 to 5 mg of the active ingredient.

Aerosol formulations are preferably arranged so that each metered dose or 'puff' delivered from a pressurised aerosol contains 0.2 mg to 2 mg of a compound of the invention, and each dose administered via capsules and cartridges in an insufflator or an inhaler contain 0.2 mg to 20 mg of a compound of the invention. The overall daily dose by inhalation with an aerosol will be within the range 1 mg to 100 mg. Administration may be several times daily, for example from 2 to 8 times, giving for example 1, 2 or 3 doses each time.

The compounds of the invention may, if desired, be administered in combination with one or more other therapeutic agents, such as analgesics, anti-inflammatory agents and anti-nauseants.

According to another aspect of the invention, compounds of general formula (I) and physiologically acceptable salts and solvates (e.g. hydrates) thereof, may be prepared by the general methods outlined below. In the following processes, $R^1$, $R^2$, $R^3$, $R^4$, $R^5$, $R^6$ and n are as defined for the general formula (I) unless otherwise specified.

One general process (A) for preparing a compound of general formula (I) comprises the step of reacting a compound of general formula (II)

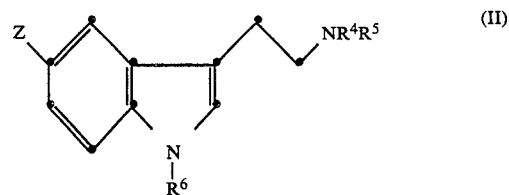

(wherein Z is a nitrile group or a reactive derivative thereof) or a salt (for example an organic or inorganic acid addition salt such as the hydrochloride, hydrobromide, maleate, sulphate or creatinine sulphate adduct) or a protected derivative thereof, with an amine of formula $R^1R^{2a}NH$ [where $R^{2a}$ represents a group $R^2$ as previously defined or a group $-(CH_2)_nNH_2$] or a salt thereof.

Compounds of general formula (II) in which Z represents a reactive derivative of a nitrile group may include compounds of the general formula (III)

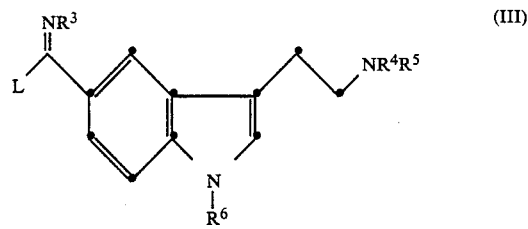

(wherein L represents a leaving group such as a halogen atom (e.g. chlorine, bromine or iodine), an alkoxy group (e.g. methoxy, ethoxy or t-butoxy) or an alkylthio group (e.g. methylthio)).

Where Z represents a reactive derivative of a nitrile group the process may be effected in a suitable reaction medium, preferably a non-aqueous medium. Suitable reaction media include amides (e.g. N,N-dimethylformamide), ethers (e.g. tetrahydrofuran), nitriles (e.g. acetonitrile), alcohols (e.g. methanol or ethanol), haloalkanes (e.g. dichloromethane) and mixtures thereof. In some instances the amine $R^1R^{2a}NH$ may itself act as a reaction solvent. The reaction may optionally be carried out in the presence of a base such as pyridine, a tertiary amine or an alkali metal carbonate such as potassium carbonate. The reaction may conveniently be effected at a temperature of from −10° to +150° C., preferably −5° to +50° C.

Where it is desired to prepare a compound of formula (I) in which R¹ and R² are both hydrogen atoms, ammonia may be used in the form of aqueous ammonia or in a solvent such as methanol or ethanol.

Where Z represents a nitrile group, the process is conveniently effected in the presence of a Lewis acid such as aluminium chloride, optionally in an inert solvent (e.g. diphenyl ether) and at temperatures of from 150° to 300° C. Alternatively the reaction may be carried out in the presence of a strong base such as sodium ethoxide and a suitable reaction medium such as an alcohol (e.g. methanol or ethanol) at a temperature in the range −10° to 100° C.

It will be understood that to prepare compounds of formula (I) wherein R² and R³ form the group —(CH$_2$)$_n$— an amine of formula R¹NH(CH$_2$)$_n$NH$_2$ should be employed. If a compound of formula (III) is used in this reaction, R³ preferably represents a hydrogen atom.

The compounds of formula (II) in which Z represents a nitrile group may be prepared by procedures such as those described in UK Patent Specification No. 2035310.

The compounds of formula (III) where L is an alkoxy group may be prepared from the compounds of general formula (II) wherein Z is a nitrile group for example, by treatment with the appropriate alkanol in the presence of hydrogen chloride, optionally in a solvent, e.g. a halogenated hydrocarbon such as dichloromethane, and conveniently at a temperature of from −10° to +30° C.

Compounds of formula (III) wherein L is an alkoxy group, halogen or an alkylthio group may be prepared from compounds of formula (IV)

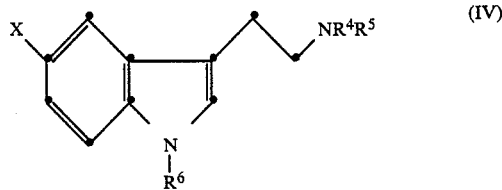

wherein X is the group CONHR⁹ or CSNHR⁹, (where R⁹ represents a hydrogen atom, a C$_{1-6}$ alkyl, C$_{3-6}$ alkenyl, C$_{1-4}$ alkoxy or C$_{2-5}$ alkoxycarbonyl group, an optionally substituted phenyl group or an optionally substituted phenyl(C$_{1-4}$)alkyl group), or a salt or protected derivative thereof.

Thus, compounds of formula (III) wherein L is an alkoxy group may be prepared by treating a compound of formula (IV) wherein X is the group CONHR⁹, with the appropriate trialkyloxonium tetrafluoroborate (e.g. triethyloxonium tetrafluoroborate) in a solvent such as a haloalkane, e.g. methylene chloride and conveniently at a temperature of −20° to +10° C.

Compounds of formula (III) wherein L is a halogen atom, such as chlorine, may be prepared by reaction of a compound of formula (IV) wherein X is the group CONHR⁹, with a phosphorus pentahalide e.g. phosphorus pentachloride or a phosphorus oxyhalide, e.g. phosphorus oxychloride, optionally in the presence of an inert solvent such as an aromatic hydrocarbon (for example, toluene).

Compounds of formula (III) wherein L is an alkylthio group such as methylthio, may be prepared by reaction of a compound of formula (IV) where X is the group CSNHR⁹, with an alkyl halide (for example methyl iodide) in a suitable solvent such as an alcohol (for example methanol).

Another general process (B) for preparing compounds of general formula (I) comprises the step of cyclisation of compounds of general formula (V)

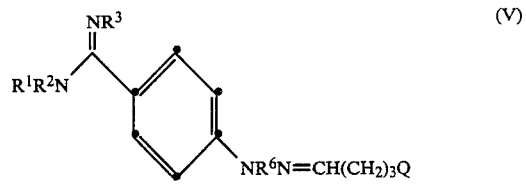

wherein Q is the group NR⁴R⁵ or a protected derivative thereof, or a leaving group such as a halogen atom (e.g. a chlorine, bromine or iodine atom) or an acyloxy group (e.g. a carboxylic acyloxy group such as acetoxy, chloroacetoxy, dichloroacetoxy, trifluoroacetoxy or p-nitrobenzoyloxy or a hydrocarbylsulphonyloxy group such as p-toluenesulphonyloxy, methanesulphonyloxy or trifluoromethanesulphonyloxy).

The reaction may conveniently be effected in aqueous or nonaqueous reaction media, and at temperatures of from 20° to 200° C., preferably 50° to 125° C.

Particularly convenient embodiments of the process are described below.

When Q represents the group NR⁴R⁵ (or a protected derivative thereof), the process is desirably carried out in the presence of polyphosphate ester in a reaction medium which may comprise one or more organic solvents, preferably halogenated hydrocarbons such as chloroform, dichloromethane, dichloroethane, dichlorodifluoromethane, or mixtures thereof. Polyphosphate ester is a mixture of esters which may be prepared from phosphorus pentoxide, diethylether and chloroform according to the method described in 'Reagents for Organic Synthesis', (Fieser and Fieser, John Wiley and Son (1967).

Alternatively the cyclisation may be carried out in aqueous or non-aqueous media, in the presence of an acid catalyst. When an aqueous medium is employed this may be an aqueous organic solvent such as an aqueous alcohol (e.g. methanol, ethanol or isopropanol) or an aqueous ether (e.g. dioxan or tetrahydrofuran) as well as mixtures of such solvents and the acid catalyst may be for example an inorganic acid such as concentrated hydrochloric or sulphuric acid. (In some cases the acid catalyst may also act as the reaction solvent). In an anhydrous reaction medium, which may comprise one or more alcohols or ethers (e.g. as described above) or esters (e.g. ethyl acetate), the acid catalyst will generally be a Lewis acid such as boron trifluoride, zinc chloride or magnesium chloride.

When Q is a leaving group (as defined previously), the reaction may conveniently be effected in a suitable solvent without adding an acid catalyst. Suitable solvents include alcohols (e.g. methanol, ethanol or isopropanol), ethers (e.g. tetrahydrofuran or dioxan), water and mixtures thereof. This process results in the formation of a compound of formula (I) wherein R⁴ and R⁵ are both hydrogen atoms.

According to a particular embodiment of this process, compounds of general formula (I) may be prepared directly by the reaction of a compound of formula (VI)

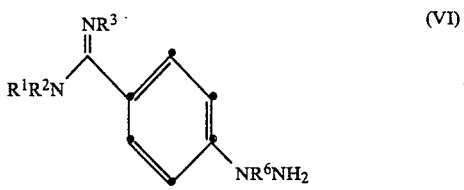

or a salt thereof, with a compound of formula (VII)

OHC(CH$_2$)$_3$Q                                  (VII)

(wherein Q is as defined above) or a salt or protected derivative thereof (such as an acetal or ketal e.g. formed with an appropriate alkylorthoformate or diol, or protected as a bisuphite addition complex), using the appropriate conditions as described above for the cyclisation of compounds (V). It will be appreciated that in this embodiment of the cyclisation process (B) a compound of general formula (V) is formed as an intermediate and may be reacted in situ to form the desired compound of general formula (I).

Compounds of general formula (V) may, if desired, be isolated as intermediates during the process for the preparation of compounds of general formula (I) wherein a compound formula (VI), or a salt thereof, is reacted with a compound of formula (VII) or a salt or protected derivative thereof, in a suitable solvent, such as an aqueous alcohol (e.g. methanol) and at a temperature of, for example, from 20° to 100° C. If an acetal or ketal of a compound of formula (VII) is used it may be necessary to carry out the reaction in the presence of an acid (for example, acetic or hydrochloric acid).

Hydrazines of formula (VI) may be prepared from the corresponding nitro compounds, using conventional procedures.

According to another general process (C), a compound of formula (I) according to the invention may be converted into another compound of the invention using conventional procedures. Such conventional techniques include alkylation, which may be effected at any position in a compound of formula (I) where one or more of R$^1$, R$^2$, R$^3$, R$^4$, R$^5$ and R$^6$ represents a hydrogen atom, and hydrogenation, which may, for example, be used to convert an alkenyl substituent into an alkyl substituent. The term 'alkylation' includes the introduction of other groups such as phenylalkyl or alkenyl groups. Thus, for example, a compound of formula (I) in which R$^1$ represents a hydrogen atom may be converted into the corresponding compound in which R$^1$ represents a C$_{1-6}$ alkyl, C$_{3-6}$ alkenyl or phenyl-C$_{1-4}$ alkyl group.

The above alkylation reactions may be effected using the appropriate alkylating agent selected from compounds of formula R$^a$X$^a$ (where R$^a$ represents a C$_{1-3}$ alkyl, C$_{1-6}$ alkyl, C$_{3-6}$ alkenyl or optionally substituted phenyl-C$_{1-4}$ alkyl group, and X$^a$ represents a leaving group such as a halide or an acyloxy group as previously defined for L), or a sulphate of formula (R$^a$)$_2$S$_4$.

The alkylation reaction may conveniently be carried out in an inert organic solvent such as an amide (e.g. dimethylformamide), an ether (e.g. tetrahydrofuran) or an aromatic hydrocarbon (e.g. toluene) preferably in the presence of a base. Suitable bases include, for example, alkali metal hydrides, such as sodium or potassium hydride, alkali metal amides such as sodium amide, alkali metal carbonates, such as sodium carbonate or an alkali metal alkoxide such as sodium or potassium methoxide, ethoxide or t-butoxide; and tetrabutylammonium fluoride. The reaction may conveniently be effected at a temperature in the range 25° to 100° C.

The alkylation may also be effected by reductive alkylation using an appropriate aldehyde or ketone (e.g. formaldehyde or acetone) in the presence of a reducing agent (e.g. an alkali metal or alkaline earth metal borohydride or cyanoborohydride, a metal hydride, or hydrogen in the presence of a catalyst such as Raney nickel or a noble metal catalyst such as platinum, platinum oxide, palladium or rhodium, which may be supported, for example, on charcoal, kieselguhr or alumina. (In the case of Raney nickel, hydrazine may also be used as the source of hydrogen). Suitable solvents for the reaction include alcohols, (e.g. ethanol or propanol); ethers (e.g. diethyl ether, dioxan or tetrahydrofuran); amides (e.g. dimethylformamide); esters (e.g. ethyl acetate) and nitriles (e.g. acetonitrile). The reaction is conveniently effected at a temperature of from −10° to +50° C., preferably −5° to +30° C.

Hydrogenation according to general process (C) may be effected using conventional procedures, for example by using hydrogen in the presence of a noble metal catalyst e.g. palladium, Raney nickel, platinum, platinum oxide or rhodium. The catalyst may be supported on for example charcoal or a homogenous catalyst such as tris(triphenylphosphine) rhodium chloride may be used. The hydrogenation will generally be effected in a solvent such as an alcohol, e.g. ethanol; an ether, e.g. dioxan; or an ester, e.g. ethyl acetate, and at a temperature in the range −20° to +100° C., preferably 0° to 50° C.

According to another embodiment of this process, a compound wherein R$^1$, R$^2$ and R$^3$ each represents hydrogen atoms may be converted into a compound wherein one of R$^1$, R$^2$ and R$^3$ represents an alkoxycarbonyl group by acylation using the appropriate acylating agent. Suitable acylating agents include compounds of formula R$^c$OCOX$^c$ wherein R$^c$ represents a C$_{1-4}$ alkyl group (e.g. ethyl) and X$^c$ represents a leaving atom or group (e.g. a halogen atom such as chlorine, bromine or iodine, or a hydrocarbylsulphonyloxy group such as p-toluenesulphonyloxy or methanesulphonyloxy). The process is optionally effected in the presence of a base (e.g. an alkali metal carbonate such as sodium or potassium carbonate or tertiary amine such as pyridine, triethylamine or diisopropylethylamine). Suitable solvents include ether (e.g. tetrahydrofuran or dioxan), amides (e.g. dimethylformamide), and haloalkanes (e.g. dichloromethane). The process is conveniently effected at a temperature of 0° to 100° C., e.g. 10° to 40° C.

It should be appreciated that in some of the above transformations it may be necessary and/or desirable to protect any sensitive groups in the molecule of the compound in question to avoid undesirable side reactions. The protecting groups used in the preparation of compounds of formula (I) are desirably groups which may readily be split off at a suitable stage in the reaction sequence, conveniently at the last stage.

Compounds of general formula (I) may thus be prepared according to another general process (D) which comprises the removal of protecting groups from a corresponding protected derivative of general formula (I).

Protecting groups used in the preparation of compounds of formula (I) may be those well known in the art, for example as described in 'Protective Groups in Organic Chemistry' Ed. J. F. W. McOmie (Plenum Press 1973) or 'Protective Groups in Organic Synthesis' by Theodora W. Greene (John Wiley & Sons 1981).

In compounds of general formula (I) wherein one or both of $R^4$, and $R^5$ represent hydrogen, the group $R^4R^5N$ may be protected for example by protonation or with a conventional amino protecting group. Such groups may include, for example, aralkyl groups, such as benzyl, diphenylmethyl or triphenylmethyl groups; and acyl groups such as N-benzyloxycarbonyl, t-butoxycarbonyl or phthaloyl. In compounds wherein $R^6$ represents a hydrogen atom the indole nitrogen may also be protected, for example by an aralkyl group such as benzyl.

Removal of any amino protecting groups present may be achieved by conventional procedures. Thus an aralkyl group such as benzyl, may be cleaved by hydrogenolysis in the presence of a catalyst (e.g. palladium on charcoal); an acyl group such as N-benzyloxycarbonyl may be removed by hydrolysis with, for example, hydrogen bromide in acetic acid or by reduction, for example by catalytic hydrogenation. The phthaloyl group may be removed by hydrazinolysis (e.g. by treatment with hydrazine hydrate) or by treatment with a primary amine (e.g. methylamine).

As will be appreciated, in some of the general processes (A) to (C) described previously it may be necessary or desirable to protect any sensitive groups in the molecule as just described. Thus, a reaction step involving deprotection of a protected derivative of general formula (I) or a salt thereof may be carried out subsequent to any of the previously described processes (A) to (C).

Thus, according to a further aspect of the invention, the following reactions in any appropriate sequence may if necessary and/or desired be carried out subsequent to any of the processes (A) to (C):
(i) removal of any protecting groups; and
(ii) conversion of a compound of general formula (I) or a salt thereof into a physiologically acceptable salt or solvate (e.g. hydrate) thereof.

Where it is desired to isolate a compound of the invention as a salt, for example as an acid addition salt, this may be achieved by treating the free base of general formula (I) with an appropriate acid, preferably with an equivalent amount, or with creatinine sulphate in a suitable solvent (e.g. aqueous ethanol).

Mixtures of enantiomers, including racemic mixtures, of compounds according to the invention may be resolved using conventional means; for example as described in 'Stereochemistry of Carbon Compounds' by E. L. Eliel. (McGraw Hill, 1962) and 'Tables of Resolving Agents' by S. M. Willen.

Physiologically acceptable equivalents of a compound of formula (I), may be prepared according to conventional methods. Thus, for example, an N-acyl derivative may be prepared using conventional acylation techniques.

The starting materials or intermediate compounds for the preparation of the compounds according to this invention may be prepared by analogous methods to those described in UK Pat. No. 2035310.

As well as being employed as the last main step in the preparative sequence, the general methods indicated above for the preparation of the compounds of the invention may also be used for the introduction of the desired groups at an intermediate stage in the preparation of the required compound. Thus, for example, the required group at the 5- position may be introduced either before or after cyclisation to form the indole nucleus. It should therefore be appreciated that in such multi-stage processes, the sequence of reactions should be chosen in order that the reaction conditions do not affect groups present in the molecule which are desired in the final product.

The invention is further illustrated by the following Examples. All temperatures are in °C.

Chromatography was carried out either in the conventional manner using silica gel (Merck, Kieselgel 60, Art. 7734 or 7747) or by flash chromatography (W. C. Still, M. Kahn and A. Mitra, J. Org. Chem. 1978, 43, 2933) on silica (Merck 9385) and thin layer chromatography (t.l.c.) on silica (Macherly-Nagel, Polygram) except where otherwise stated. The following abbreviations define the eluent used for chromatography and t.l.c.

| | | |
|---|---|---|
| (A) | Dichloromethane-ethanol-0.88 ammonia | 50:8:1 |
| (B) | Ethyl acetate-isopropanol-water-0.88 ammonia | 25:15:8:1 |
| (C) | Ethyl acetate-isopropanol-water | 25:15:8 |
| (D) | Dichloromethane-ethanol-0.88 ammonia | 200:8:1 |
| (E) | Dichloromethane-ethanol-0.88 ammonia | 30:8:1 |
| (F) | Dichloromethane-ethanol-0.88 ammonia | 100:8:1 |
| (G) | Isopropanol-diethylether-water-0.88 ammonia | 20:20:8:1 |
| (H) | Isopropanol-diethylether-water-0.88 ammonia | 30:60:8:1 |
| (J) | Dichloromethane-ethanol-0.88 ammonia | 25:8:1 |

INTERMEDIATE 1

3-[2-[(Phenylmethyl)amino]ethyl]-1H-indole-5-carbonitrile

Freshly distilled benzaldehyde (2.96 g) was added to a solution of 3-(2-aminoethyl)-1H-indole-5-carbonitrile (5 g) in absolute ethanol (120 ml). The mixture was heated at reflux for 2 h before cooling to 10°. Sodium borohydride (1 g) was added and the suspension stirred for 2 h. The mixture was reduced to dryness and the residue recrystallised from a mixture of toluene and petroleum ether (b.p. 60°–80°). The solid was washed well with water and dried to give the title compound as a powder (3.8 g), m.p 99°–101°.

INTERMEDIATE 2

3-[2-[Ethyl(phenylmethyl)amino]ethyl]-1H-indole-5-carbonitrile

A suspension of Intermediate 1 (1 g), diethyl sulphate (0.83 g) and potassium carbonate (1 g) in a mixture of dry dimethylformamide (10 ml) and distilled tetrahydrofuran (50 ml) was stirred at room temperature for 72 h. The tetrahydrofuran was removed under reduced pressure and the residue diluted with water (ca 100 ml). The emulsion was extracted with chloroform (3×25 ml) and the extracts washed well with water (4×25 ml), dried (Na$_2$SO$_4$) and concentrated. The residual oil was chromatographed on a silica column eluting with 5% methanol in chloroform to give the title compound as an oil (0.35 g). T.l.c. silica; 5% methanol in chloroform, Rf. 0.4.

INTERMEDIATE 3

Ethyl 3-[2-(1,3-dihydro-1,3-dioxo-2H-isoindol-2-yl)ethyl]-1H-indole-5-carboximidate hydrochloride Dry hydrogen chloride was bubbled through a suspension of 3-[2-(1,3-dihydro-1,3-dioxo-2H-isoindol-2-yl)ethyl]-1H-indole-5-carbonitrile (2 g) in dry ethanol for 24 h. Dry ether (75 ml) was added and the reaction mixture was stirred for 8 h. The solid product was collected, washed with dry ether, and dried in vacuo over calcium chloride to give the title compound (1.6 g). The mass spectrum showed a molecular ion of m/e 361. $C_{21}H_{19}N_3O_3$ required m/e 361.

The intermediates in Table I were prepared by a similar method to Intermediate 3. The nitrile starting material for the preparation of Intermediate 6 was obtained by stirring a solution of 3-[2-[N-methyl-N-(phenylmethyl)amino]ethyl]-1H-indole-5-carbonitrile (2.5 g) in absolute ethanol (50 ml) in a hydrogen atmosphere with pre-reduced moistened 10% palladium on charcoal (2.5 g). One equivalent of hydrogen was absorbed over a period of 21 h and the resulting solution was then filtered (Hyflo), evaporated and the residue crystallised from ethyl acetate to yield the desired nitrite title compound (1.23 g) m.p. 138°-140°.

INTERMEDIATE 10

Methyl 3-[2-[[(Phenylmethoxy)carbonyl]amino]ethyl]-1H-indole-5-carboximidothioate hydroiodide A solution of Intermediate 9 (6.5 g) and methyl iodide (30 ml) in ethanol (50 ml) was stirred at room temperature for 4 h. After 10 min. a solid began to precipitate. The reaction was diluted with ether (350 ml) and stirred overnight. The solid was collected, washed with ether and dried in vacuo at 50° for 16 h to afford the title compound (8.1 g) as a finely divided solid, m.p. 187°-192° (decomp).

INTERMDIATE 11

3-[2-(Dimethylamino)ethyl]-1H-indole-5-carbothioamide

A solution of 3-[2-(dimethylamino)ethyl]-1H-indole-5-carbonitrile (13.0 g) and triethylamine (50 ml) in dimethylformamide (300 ml) was stirred for 2 h whilst gaseous hydrogen sulphide was bubbled through it. More triethylamine (10 ml) was added and the solution was stirred at room temperature for 2 days, then evaporated in vacuo to give an oil (15 g) which was partitioned between ethyl acetate (500 ml) and water (3×250 ml). The organic layer was dried ($MgSO_4$)

TABLE I

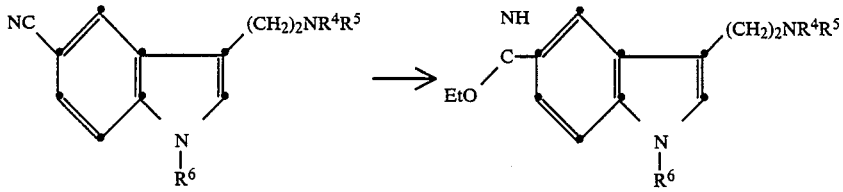

| Intermediate No. | $NR^4R^5$ | $R^6$ | Weight of Starting material (g) | Time of Reaction with HCl (h) | Yield (g) | |
|---|---|---|---|---|---|---|
| 4 | $NH_2$ | H | 3 | 5 | 4.7 | T.l.c. Alumina Rf. 0.75 |
| 5 | $NH_2$ | $CH_3$ | 0.5 | 6 | 0.8 | m.p. 148-153° |
| 6 | $NHCH_3$ | H | 0.8 | 7 | 0.96 | — |
| 7 | $N(C_2H_5)CH_2Ph$ | H | 0.35 | 3 | 0.4 | m.p. 140-144° |
| 8 | $N(CH_3)_2$ | H | 1.66 | 7 | 2.33 | — |

INTERMEDIATE 9

Phenylmethyl [2-[5-(aminothioxomethyl)-1H-indol-3-yl]ethyl]carbamate compound with ethyl acetate (5:1)

Hydrogen sulphide gas was bubbled with stirring at room temperature into a solution of Intermediate 12 (9.0 g) and triethylamine (6.75 ml) in dry dimethylformamide (225 ml). The gas was bubbled into the reaction mixture for 16 h during the first 24 h; 5 h during the second 24 h and 3 h in the third 24 h (another portion of triethylamine, 6.75 ml, was added). On the fourth day the reaction was poured into water (500 ml) and the mixture was extracted with ethyl acetate (5×200 ml). The combined extracts were washed with water (5×100 ml). The combined extracts were washed with (5×100 ml), dried ($Na_2SO_4$), filtered and evaporated to give an oil which became a foam in vacuo (9.5 g). This material (8.5 g) was filtered through a column of silica gel (Merck Type 60) using ethyl acetate, petroleum spirit (2:1) as eluent, and the appropriate fraction evaporated to afford the title compound (7.5 g) as a powdered foam, m.p. 59°-65°.

pre-absorbed onto silica and purified by flash chromatography (A). The appropriate fractions were combined, concentrated in vacuo and triturated with ether (250 ml) to give the title compound (12.0 g) as a solid, m.p. 155°.

INTERMEDIATE 12

Phenylmethyl [2-(5-cyano-1H-indol-3-yl)ethyl]carbamate

A solution of diisopropylethylamine (6.11 g), in dry tetrahydrofuran (20 ml) was added to a stirred solution of 5-cyano-1H-indole-3-ethanamine (7.3 g) in dry tetrahydrofuran (250 ml). A solution of benzyl chloroformate (7.73 g) in dry tetrahydroguran (20 ml) was then added at room temperature. After stirring for 1.5 h the reaction mixture was partitioned between water (100 ml). The aqueous layer was separated and extracted with ethyl acetate (4×50 ml). The combined organic solutions were washed with water (100 ml), dried ($MgSO_4$) filtered and evaporated to afford an oily solid which was washed with petroleum spirit (b.p. 60°-80°, 100 ml) and then recrystallised from a mixture of ethyl acetate (50 ml) and petroleum spirit (b.p. 60°–80°, 35 ml) to afford the title compound (9.46 g), m.p. 127.5°–129°.

EXAMPLE 1

3-(2-Aminoethyl)-N-methyl-1H-indole-5-carboximidamide compound with creatinine, sulphuric acid, water and ethanol (6:27:18:12:2)

A solution of Intermediate 3 (1.1 g) in dry ethanolic methylamine (30 ml) was kept at 20° for 3 h and then concentrated to dryness. The residue was absorbed onto alumina and elution (B) gave the tryptamine as an oil which was taken up in 80% aqueous ethanol (20 ml) and treated with 1 ml of an aqueous solution of 2M creatinine and sulphuric acid. Addition of ethanol produced a solid which was filtered off. The filtrate was kept at 0° for 24 h and the solid which separated was collected, washed with ethanol and dried to give the title compound (0.27 g), m.p. 230°–235°, Analysis Found: C, 34.75; H, 5.35; N, 22.8; $C_{12}H_{16}N_4.4.5C_4H_7N_3O. 3H_2SO_4.2H_2O. 0.33C_2H_5OH$ requires: C, 35.05; H, 5.35; N, 22.9%.

EXAMPLE 2

3-(2-Aminoethyl)-1H-indole-5-carboximidamide compound with creatinine, sulphuric acid, water and ethanol (4:8:8:6:3)

(i) 3-[2-(1,3-Dihydro-1,3-dioxo-2H-isoindol-2-yl)ethyl]-1H-indole-5-carboximidamide A mixture of Intermediate 3 (2 g) and a saturated solution of ammonia in ethanol (50 ml) was stirred at 20° for 3 days. The solution was concentrated and the residual solid was absorbed onto alumina. Elution (B) gave the title compound as a solid (0.62 g), m.p. 206°–209°.

(ii) 3-(2-Aminoethyl)-1H-indole-5-carboximidamide compound with creatinine, sulphuric acid, water and ethanol (4::8:8:6:3)

The product of Stage (i) (0.6 g) was added to benzylamine (2 ml) and ethanol (20 ml) and the mixture was stirred at 20° for 3 days. The resulting solution was concentrated to dryness and the residue was absorbed onto alumina. Elution (B) gave the tryptamine as an oil which was dissolved in ethanol (10 ml). Addition of dry ether gave a solid (0.3 g), which was taken up in 80% aqueous ethanol and treated with 0.5 ml of an aqueous solution of 2M creatinine and sulphuric acid. Addition of ethanol (50 ml) afforded the title compound as a solid (0.15 g), m.p. 236°–240°.

Analysis Found: C, 35.65; H, 5.35; N, 20.00% $C_{11}H_{14}N_4.2C_4H_7N_3O. 2.OH_2SO_4. 1.5H_2O. 0.75C_2H_5OH$ requires: C, 35.90; H, 5.25; N, 20.40%

EXAMPLE 3

3-(2-Aminoethyl)-N-hydroxy-1H-indole-5-carboximidamide dimaleate (i) 3-[2-(1,3-Dihydro-1,3-dioxo-2H-isoindol-2-yl)ethyl]-N-hydroxy-1H-indole-5-carboximidamide A mixture of Intermediate 3 (1.7 g), hydroxylamine hydrochloride (1.2 g) and anhydrous potassium carbonate (2.35 g) in dry acetonitrile was stirred at 50° for 2 h, filtered, the filtrate was concentrated and the residue crystallised from ethyl acetate-methanol to give the title compound as a solid, m.p. 168°–170° (1.06 g).

(ii) 3-(2-Aminoethyl)-N-hydroxy-1H-indole-5-carboximidamide dimaleate

The product of Stage (i) (1.5 g) was taken up in 33% ethanolic methylamine (50 ml) and after 3 h the solution was evaporated to dryness. The residue was absorbed onto silica and elution (B) gave the tryptamine as a foam (0.6 g). The foam and maleic acid (0.8 g) were taken up in ethanol (30 ml), the solution was warmed and treated with dry ether. A gum separated which on trituration with dry ether gave the title compound as a crystalline solid, (0.7 g), m.p. 115°–119°.

Analysis Found: C, 50.75; H, 4.50; N, 12.30; $C_{11}H_{14}N_4O.2C_4H_4O_4$ requires: C, 50.65; H, 4.85; N, 12.45%

EXAMPLE 4

3-(2-Aminoethyl)-N-ethyl-1H-indole-5-carboximidamide compound with hydrogen chloride, ethyl acetate, and water (10:20:1:5)

A 33% solution of ethylamine in ethanol (50 ml) was added to a suspension of Intermediate 4 (1 g) in ethanol (10 ml). This solution was kept at room temperature for 24 h, and evaporated in vacuo. The resulting foam was dissolved in absolute ethanol and re-evaporated, three times. The foam obtained was dissolved in absolute ethanol (25 ml) and the solution was diluted by the dropwise addition with stirring of ethyl acetate (40 ml). An oil precipitated, which on extended scratching became a finely divided solid. This was collected, washed with ethyl acetate and dried in vacuo at 50° for 16 h to afford the title compound (0.81 g), m.p. 245°–255° (decomp. begins at 235°).

Analysis Found: C.49.70; H, 6.76; N, 17.21; Cl, 22.03 $C_{13}H_{18}N_4.2HCl.0.1C_4H_8O_2.05H_2O$ requires: C, 50.13; H, 6.84; N, 17.45; Cl, 22.23%

EXAMPLE 5

3-(2-Aminoethyl)-N-(phenylmethyl)-1H-indole-5-carboximidamide hydroiodide (i) Methyl 3-[2-(1,3-dihydro-1,3-dioxo-2H-isoindol-2-yl)ethyl]-1H-indole-5-carboximido-thioate hydroiodide Methyl iodide (5 ml) was added to a well-stirred suspension of 3-[2-(1,3-dihydro-1,3-dioxo-2H-indole-5-carbothioamide (1 g) in absolute ethanol (25 ml). The mixture was stirred for 2 h at room temperature by which time a homogoneous solution was obtained. Diethyl ether (100 ml) was then added steadily. A bright yellow solid precipitated. It was collected, washed with ether and dried in vacuo at 50° to yield the title compound (1.3 g).

(ii) 3-(2-Aminoethyl)-N-(phenylmethyl)-1H-indole-5-carboximidoimide hydroiodide˙

Benzylamine (1.6 g) in absolute ethanol (25 ml) was added to a stirred suspension of the product of stage (2.45 g) in absolute ethanol (100 ml). Further benzylamine (1.6 g) was added after 8 h, 25 h, 7 days, 7.5 days and 16 days. The mixture was evaporated to dryness and the residue purified by column chromatography on alumina (C) to give the title compound as a glass (0.6 g), m.p. 120°–130°.

Analysis Found: C, 49.77; H, 5.2; N, 11.46 $C_{18}H_{20}N_4.0.33C_2H_6O.0.67C_2H_4O_2.0.01C_4H_{10}O.H1.0.5-H_2O$ requires: C, 49.58; H, 5.56; N, 11.54%

EXAMPLE 6

3-(2-Aminoethyl)-N-phenyl-1H-indole-5-carboximidamide maleate (i) Phenylmethyl [2-[5-[amino(phenylimino)methyl]-1H-indol-3-yl]ethyl]-carbamate compound with ethyl acetate (4:1)

A suspension of Intermediate 10 (0.495 g) in ethanol (10 ml) containing aniline (0.186 g) was stirred at room temperature for 3 days during which period it was heated at 60° for 30 min. The resulting solution was evaporated. The residue was partitioned between ethyl acetate (10 ml) and 8% sodium hydrogen carbonate (10 ml). The aqueous phase was extracted with ethyl acetate (10 ml). The combined organic extracts were washed with water (2×10 ml), dried ($Na_2SO_4$) filtered and evaporated. The product was purified by chromatography an alumina using ethyl acetate as eluent, and appropriate fractions combined and evaporated to afford the title compound as a foam, (0.31 g), m.p. ca. 80°.

(ii) 3-(2-Aminoethyl)-N-phenyl-1H-indole-5-carboximidamide maleate

The product of Stage (i) (0.8 g) was stirred in ethanol (50 ml) under a hydrogen atmosphere and over 10% palladium on carbon catalyst (0.8, 50% aqueous paste). After 3 h, the catalyst was filtered off [hydrogen uptake=250 ml] and the filtrate evaporated to dryness, to give an oil which was evaporated to a foam (0.5 g), m.p. 80°-92°. A portion of the foam (0.3 g) in hot ethyl acetate was added to an equivalent amount of maleic acid in hot ethyl acetate. The mixture was cooled and the solid collected, washed with ethyl acetate and dried in vacuo at 60° for 2 days to give the title compound, m.p. >110° (decomposes).

Analysis Found: C, 61.06; H, 5.74; N, 12.31 $C_{17}H_{18}N_4.C_4H_4O_4.0.33C_4H_8O_2.H_2O$ requires: C, 60.72; H, 6.08; N, 12.69%

EXAMPLE 7

3-(2-Aminoethyl)-N,1-dimethyl-1H-indole-5-carboximidamide dihydrochloride

A solution of methylamine in ethanol (33%, 8.5 ml) was added to Intermediate 5 (0.4 g) in absolute ethanol (20 ml), the mixture was stirred at room temperature for 3 h, and then reduced to dryness. The residue was redissolved in absolute ethanol (25 ml) and evaporated, three times. The oil produced was dissolved in a minimum quantity of cold ethanol, ethyl acetate was added and the solid produced was dried to give the title compound as a powder, (0.2 g), m.p. 125°-128° (decomp.).

Analysis Found: C, 47.35; H, 7.12; N, 16.06 $C_{13}H_{18}N_4.2HCl.0.3C_2H_6O.1.5H_2O$ requires: C, 47.47; H, 7.27; N, 16.28%

EXAMPLE 8

N-Methyl-3-[2-(methylamino)ethyl]-1H-indole-5-carboximidamide dihydrochloride

A solution of Intermediate 6 (0.88 g) in ethanol (10 ml) was treated with methylamine (~30% solution in ethanol; 30 ml) stirred at room temperature for 4 h and then evaporated. The resulting solid was redissolved in ethanol (30 ml) and the solvent removed in vacuo, three times. The residual solid was triturated with ethanol (3-5 ml) to give the title compound as a solid, m.p. >250° (0.24 g).

Analysis Found: C, 51.6; H, 6.9; N, 18.29; Cl, 23.35 $C_{13}H_{18}N_4.2HCl$ requires: C, 51.49; H, 6.65; N, 18.48; Cl, 23.38%

EXAMPLE 9

3-[2-(Ethylamino)ethyl]-N-methyl-1H-indole-5-carboximidamide dihydrochloride (i) 3-[2-[Ethyl(phenylmethyl)amino]ethyl]-N-methyl-1H-indole-5-carboximidamide dihydrochloride Intermediate 7 (0.3 g) was added to a solution of methylamine in ethanol (33% w/w, 10 ml), the mixture was stirred for 4 h at room temperature and then reduced to dryness. Fresh ethanol (15 ml) was added and the solution evaporated, three times. The oil obtained was crystallised from a mixture of ethanol and ethyl acetate to give the title compound as needles (0.19 g), m.p. 168°-170°.

(ii) 3-[2-(Ethylamino)ethyl]-N-methyl-1H-indole-5-carboximidamide dihydrochloride The product of Stage (i) (0.18 g) dissolved in absolute ethanol (25 ml) was hydrogenated at room temperature and pressure over 10% palladium oxide on charcoal. After the uptake of hydrogen had ceased the catalyst was removed by filtration and the filtrate reduced to dryness. The residue was recrystallised from a mixture of ethanol and ethyl acetate to give the title compound as a powder (0.1 g), m.p. 244°-246°.

Analysis Found: C, 48.24; H, 6.85; N, 15.67; $C_{14}H_{20}N_4.2HCl.1.75H_2O$ requires: C, 48.16; H, 7.16; N, 16.05%

EXAMPLE 10

Ethyl [[3-(2-aminoethyl)-1H-indol-5-yl]iminomethyl]carbamate dimaleate (i) Ethyl 3-[2-[[(phenylmethoxy)carbonyl]amino]ethyl]-1H-indole-5-carboximidate hydrochloride Benzylchloroformate (072 ml) was added dropwise to an ice cold solution of Intermediate 4 (1.4 g) and diisoproylethylamine (2.48 ml) in freshly distilled tetrahydrofuran (50 ml). The mixture was stirred at room temperature for 3 h and then reduced to dryness. The residue was stirred with diethyl ether and the solution decanted off. The residue was crystallised from a mixture of ethyl acetate and methanol (0.5% metahnol) to give the title compound as a powder (0.7 g) m.p. 147°-149°.

(ii) Phenylmethyl [2-[5-(aminoiminomethyl)-1H-indol-3-yl]ethyl]carbamate hydrochloride hydrate A solution of the product of Stage (i) (0.1 g) in methanolic ammonia solution (25 ml) was stirred at room temperature for 72 h. The mixture was reduced to dryness and the residual oil triturated with a mixture of ethyl acetate and ethanol to give the title compound as a powder (0.06 g), m.p. 248°-250°.

Analysis Found: C, 58.1; H, 5.5; N, 13.9; $C_{19}H_{20}N_4O_2.HCl.H_2O$ requires: C, 58.4; H, 5.9; N, 14.3%

(iii) Phenylmethyl [2-[5-[[(ethoxycarbonyl)amino]iminomethyl]-1H-indol-3-yl]ethyl]carbamate Ethyl chloroformate (0.44 ml) was added slowly to a suspension of the product of Stage (ii) (0.8 g) and diisopropylethylamine (1.0 ml) in freshly distilled tetrahydrofuran (50 ml). The mixture was stirred at room temperature for 24 h and then reduced to dryness. The residue was chromatographed on silica (D) to give the title compound as an oil (0.4 g). T.l.c. $SiO_2$: ethyl acetate, Rf. 0.80 (Ceric).

(iv) Ethyl [[3-(2-aminoethyl)-1H-indol-5-yl]iminomethyl]carbamate dimaleate

A solution of the product of Stage (iii) (0.35 g) in absolute ethanol (25 ml) was hydrogenated over 10% palladium oxide on charcoal (50% paste with water 0.1 g) at room temperature and pressure. When the uptake of hydrogen had ceased the catalyst was removed by filtration and the filtrate reduced to dryness. The residue was chromatographed on silica (E). The residual oil (100 mg) was dissolved in ethanol (5 ml) and a solution of maleic acid (43 mg) in ethyl acetate (2 ml) added. The solution was diluted with diethyl ether until a cloudy emulsion was observed. The precipitate formed on scratching was collected and dried to give the title compound as a powder (44 mg) m.p. 139°–140°.

Analysis Found: C, 50.7; H, 5.1; N, 10.5; $C_{14}H_{18}N_4O_2.2C_2H_4O_4.H_2O$ requires: C, 50.4; H, 5.3; N, 10.7%

EXAMPLE 11

Ethyl 4-[[[3-(2-aminoethyl)-1H-indol-5-yl]iminomethyl]amino]-benzoate dimaleate (i) Ethyl 4-[[[3-[2-(1,3-dihydro-1,3-dioxo-2H-isoindol-2-yl)ethyl]-1H-indol-5-yl]iminomethyl]amino]benzoate A mixture of 3-[2-(1,3-dihydro-1,3-dioxo-2H-isoindol-2-yl)ethyl]-1H-indole-5-carbonitrile (1 g) and ethyl-4-aminobenzoate p-toluene sulphonic acid salt (1.12 g) was heated at 165° for 3 h then cooled and dissolved in ethanol, reduced to dryness and the residue was chromatographed on silica (F). The required fractions were collected and reduced to dryness to give the title compound (0.4 g) m.p. 110°.

(ii) Ethyl-4-[[[3-(2-aminoethyl)-1H-indol-5-yl]iminomethyl]amino]benzoate dimaleate A mixture of the product of Stage (i) in absolute ethanol (16 ml) and methylamine in ethanol (33% w/w 8 ml) was stirred at room temperature for 1.5 h. The solution was diluted with 8% sodium bicarbonate solution (ca 50 ml) and the mixture extracted with ethyl acetate (3×20 ml). The extracts were dried ($Na_2SO_4$), reduced to dryness under vacuo and the residue chromatographed on silica (A). The required fractions were collected and reduced to dryness. The residue (71 mg) was dissolved in a minimum quantity of absolute ethanol and a solution of maleic acid (47 mg) in ethanol (2 ml) added. The mixture was reduced to dryness and the foam obtained stirred with dry diethyl ether (ca 5 ml).

The resulting solid was collected and dried to give the title compound as a powder (78 mg), m.p. 100°–105°.

N.m.r. (DMSO) indicated presence of 25% EtOH.

Assay Found: C, 55.4; H, 5.0; N, 8.8; $C_{20}H_{22}O_2.C_8H_8O_8.0.25C_2H_5OH.0.75H_2O$ requires: C, 55.35; H, 5.4; N, 9.2%

EXAMPLE 12

3-[2-(Dimethylamino)ethyl]-N-(4-ethoxyphenyl)-1H-indole-5-carboximidamide maleate A mixture of 3-[2-(dimethylamino)ethyl]-1H-indole-5-carbonitrile (1 g), and 4-ethoxyaniline (1.53 g) was heated at 180° C. for 6 h. The cooled mixture was chromatographed on silica (A) and appropriate fractions were evaporated to dryness. The residue (0.13 g) was dissolved in hot isopropanol (2 ml) and a hot solution of maleic acid (43 mg) in isopropanol (1 ml) added. The solution was stirred vigorously while cooling and the resulting solid was collected and dried to give the title compound as a powder (0.1 g) with m.p. 107°–111°.

Assay Found: C, 59.8; H, 6.5; N, 10.6. $C_{21}H_{26}N_4O.C_4H_4.2H_2O$ requires C, 59.8; H, 6.8; N, 11.2%.

EXAMPLE 13

3-[2-(Dimethylamino)ethyl]-N-ethyl-1H-indole-5-carboximidamide dihydrochloride (i) Methyl 3-[2-(dimethylamino)ethyl]-1H-indole-5-carboximidothioate hydroiodide hydrochloride Ethereal hydrogen chloride (100 ml) was added to a solution of Intermediate 11 (12 g) in methanol (500 ml) and after 30 min the solvent was removed in vacuo. The resulting solid was dissolved in methanol (500 ml), methyl iodide (68 g) was added and the reaction mixture was stirred at room temperature for 24 h in a sealed flask. The mixture was concentrated in vacuo to give a solid which was triturated with ethyl acetate (250 ml) to give the title compound as a powder (20.3 g) m.p. 198°–200°.

(ii) 3-[2-(Dimethylamino)ethyl]-N-ethyl-1H-indole-5-carboximidamide dihydrochloride The product of Stage (i) (1.0 g) was suspended in chloroform (25 ml) and acetic acid (0.5 ml) was added, followed by ethylamine (0.2 g) in chloroform (10 ml). The solution was stirred at room temperature for 3 h. The resulting suspension was collected, washed with diethyl ether (1 l) and dried in vacuo at 20° for 18 h to give a solid (0.5 g) which was recrystallised from methanol-ethyl acetate (1:3) to give the pure title compound as a solid (0.09 g), m.p. 261°–263°

Analysis Found: C, 51.9; H, 7.4; N, 16.0; Cl, 21.0. $C_{15}H_{22}N_4.2HCl.0.75H_2O$ C, 52.2; H, 7.4; N, 16.2; Cl, 20.6%.

EXAMPLE 14

4-[[[3-(2-aminoethyl)-1H-indol-5-yl]-iminomethyl]amino]-N-methylbenzenemethanesulphonamide (i)

Phenylmethyl[2-[5-[[[4-[[(methylamino)sulphonyl]methyl]phenyl]amino]imino]methyl]-1H-indol-3-yl]ethyl]-carbamate A suspension of Intermediate 10 (2.508 g) in absolute ethanol (50 ml) containing 4-amino-N-methylbenzenemethanesulphonamide (1.51 g) was stirred at reflux under nitrogen for 2 h. After stirring at room temperature overnight (16 h) followed by heating at reflux for a further 5 h, the solution was cooled, concentrated in vacuo and the residue purified by column chromatography on deactivated alumina (15% $H_2O$ w/w). Elution with ethyl acetate-ethanol (15:1) gave the title compound as a foam (0.47 g) m.p. 63°–65° (glass).

(ii)

4-[[[3-(2-aminoethyl)-1H-indol-5-yl]iminomethyl]amino]-N-methylbenzenemethanesulphonamide A suspension of 10% palladium on charcoal (217 mg of a 50% paste with water) in ethanol (25 ml) was stirred under a hydrogen atmosphere at room temperature and pressure for 1 h. A solution of the product of Stage (i) (210 mg) in ethanol (25 ml) was added and the mixture stirred for 2 h. A further portion of palladium catalyst (200 mg of a 50% paste with water) was added and the reaction left stirring overnight (15 h). After addition of another portion of catalyst (100 mg of a 50% paste with $H_2O$) and stirring for 5.5 h the reaction mixture was filtered and the filtrate concentrated under reduced pressure. The residue (135 mg) was purified by chromatography on silica (E) to afford the title compound as a foam (79 mg) m.p. 124°–128° (decomp.).

EXAMPLE 15

4-[[[3-(2-aminoethyl)-1H-indol-5-yl]iminomethyl]amino]benzeneacetamide dihydrochloride (i) Phenylmethyl N-[2-[5-[[[4-(2-amino-2-oxoethyl)phenyl]amino]iminomethyl]-1H-indol-3-yl]ethyl ] carbamate (4-Aminophenyl)acetamide (1.1 g) and Intermediate 10 (2.5 g) in absolute ethanol (50 ml) were heated at reflux in an atmosphere of nitrogen for 5 h. The solution was allowed to cool, the solvent was removed under reduced pressure in the presence of silica, and the impregnated silica was applied as a plug to a silica column. Elution with ethyl acetate-ethanol (10:1) followed by eluent (H) gave a foam which was triturated with dry ether to afford the title compound as a solid (2.02 g) m.p. 138°–140°.

(ii)

4-[[[3-(2-aminoethyl)-1H-indol-5-yl]iminomethyl]amino]benzeneacetamide dihydrochloride A suspension of 10% palladium on charcoal (939 mg of a 50% paste with water) in absolute ethanol (50 ml) was stirred at room temperature under one atmosphere of hydrogen for 20 min. The product of Stage (i) (824 mg) in absolute ethanol (30 ml) was added and the reaction mixture stirred for 17 h. The catalyst was removed by filtration through 'hyflo' and the filtrate concentrated under reduced pressure to give a solid. Purification by 'flash' chromatography (J) and (G) gave the free base as a foam. (384 mg). This was dissolved in absolute ethanol (5 ml), the solution filtered, and ethereal HCl added to the filtrate dropwise (to pH1). The resulting precipitate was filtered off, washed with ether (80 ml), dried under vacuum at 50° for 20 h, to afford the title compound as a crystalline solid (330 mg), m.p. 259°–260°.

Analysis Found: C, 54.3; H, 6.0; N, 16.3; $C_{19}H_{21}N_5O.2HCl.0.8H_2O$ requires: C, 54.0; H, 5.9; N, 16.6%

EXAMPLE 16

5-(4,5-Dihydro-1H-imidazol-2-yl)-1H-indole-3-ethanamine dimaleate

A mixture of Intermediate 4 (1.5 g), ethylene diamine (0.44 g) and potassium carbonate (1.35 g) in dry ethanol (75 ml) was stirred under a nitrogen atmosphere for 20 h. The mixture was concentrated to dryness and the residue was absorbed onto alumina. Elution (B) afforded the tryptamine as an oil. The oil and maleic acid (1.0 g) were taken up in ethanol (20 ml) and dry ether (150 ml) was added. A sticky solid separated which on trituration with dry ether gave the title compound as a powder, m.p. 134°–137° (1.2 g).

Analysis Found: C, 51.54; H, 5.12; N, 11.65; $C_{13}H_{16}N_4.2C_4H_4.1.5H_2O$ requires: C, 51.74; H, 5.58; N, 11.49%

Examples 17–20 were prepared according to the general method of Example 16, using the conditions given in Table II, and the appropriate amine starting material, i.e. 1,3-diaminopropane in Example 17 and ethylenediamine in Examples 18, 19 and 20.

EXAMPLE 17

5-(1,4,5,6-Tetrahydro-2-pyrimidin-yl)-1H-indole-3-ethanamine dimaleate hemihydrate m.p. 143°–145°.

Analysis Found: C, 54.74; H, 5.48; N, 11.49; $C_{14}H_{18}N_4.2C_4H_4O_4.0.5H_2O$ requires: C, 54.65; H, 5.62; N, 11.58%

EXAMPLE 18

5-(4,5-Dihydro-1H-imidazol-2-yl)-N,N-dimethyl-1H-indole-3-ethanamine compound with ethyl acetate m.p. 54°–58°.

Analysis Found: C, 68.14; H, 7.87; N, 19.88; $C_{15}H_{20}N_4.0.35C_4H_8O_2$ requires: C, 68.62; H, 7.95; N, 19.53%

EXAMPLE 19

5-(4,5-Dihydro-1H-imidazol-2-yl)-N-methyl-1H-indole-3-ethanamine hemidydrate m.p. 142°–145°

Analysis Found: C, 67.05; H, 7.41; N, 22.02; $C_{14}H_{18}N_4O.5H_2O$ requires: C, 66.85; H, 7.56; N, 22.28%

EXAMPLE 20

5-(4,5-Dihydro-1-methyl-1H-imidazol-2-yl)-1H-indole-3-ethanamine compound with maleic acid and water m.p. 154°–156°.

Analysis Found: C, 56.3; H, 6.2; N, 12.9; $C_{14}H_{18}N_4.1.5C_4H_4O_4, 0.5H_2O$ requires: C, 56.4; H, 5.9; N, 13.2%

TABLE II

| Example No. | Intermediate No. | Wt. (g) | Wt. of amine (g) | Wt. of K₂CO₃ (g) | Time (h) | Eluent | Salt Formation | Yield (g) |
|---|---|---|---|---|---|---|---|---|
| 17 | 4 | 1.5 | 0.55 | 1.35 | 18 | Ethyl acetate/ methanol (1:1) | maleic acid 0.67 g, methanol (4 ml) ether 100 ml | 0.95 |
| 18 | 8 | 1.2 | 0.37 | 1.0 | 17.5 | — | — | 0.64 |
| 19 | 6 | 0.4 | 0.13 | 0.35 | 24 | — | — | 0.24 |
| 20 | 4 | | 0.37 | 0.91 | 24 | (F) | maleic acid 0.47 g, methanol, ethyl acetate | 0.070 |

EXAMPLE 21

5-(1,4,5,6-Tetrahydro-2-pyrimidin-yl)-1H-indole-3-ethanamine dihydrochloride (i) 1,4,5,6-tetrahydro-2-(4-nitrophenyl)-pyrimidine 4-Nitrobenzonitrile (17.76 g) was added to a solution of sodium metal (0.138 g) in dry ethanol (150 ml) at room temperature, and the mixture was stirred for 6 h. To the suspension was added 1,3-diaminopropane (8.88 g) and the mixture was heated under reflux for 4 days. Evaporation of the solvent under reduced pressure gave a solid which was dissolved in hot ethyl acetate (450 ml). The solution was extracted with 2N hydrochloric acid (90 ml, 20 ml). The combined acidic extracts were washed with ethyl acetate (100 ml) and then basified with 5N sodium hydroxide (60 ml). The emulsion was extracted into hot ethyl acetate (250 ml, 2×100 ml), the organic extracts were combined, reduced to about 250 ml by evaporation and hot cyclohexane (125 ml) was added. On cooling the title compound deposited as needles (17.7 g), m.p. 168°-172°.

(ii) 4-(1,4,5,6-Tetrahydro-2-pyrimidinyl)benzenamine dihydrochloride

A solution of the product of Stage (i) (20.5 g) in ethanol (150 ml) containing 2N hydrochloric acid (150 ml) was stirred in the presence of 10% palladised charcoal (2.0 g) under an atmosphere of hydrogen, until uptake ceased. The suspension was filtered through a pad of 'hyflo', the pad was washed with 50% aqueous ethanol (200 ml) and the combined filtrates evaporated under reduced pressure. Crystallisation of the residue from methanol-isopropyl acetate [1:1] (300 ml) gave the title compound as a powder (23.7 g), m.p.>300°.

(iii) 2-[4-(1,4,5,6-Tetrahydro-2-pyrimidin-yl)phenyl]hydrazinesulphonic acid hemihydrate To a stirred suspension of the product of Stage (ii) (18.0 g) in 2N hydrochloric acid (36.6 ml) at −5° was added to a solution of sodium nitrite (5.05 g) in water (11 ml) keeping the temperature below 0°. After stirring for a further 15 min, the solution was added to a stirred solution of sodium sulphite (23.05 g) and sodium acetate (9.95 g) in water (220 ml) at −5°. A solid deposited and the mass was stirred at −5° for a further 15 min, then warmed to room temperature over 1 h. Concentrated hydrochloric acid (25 ml) was added, the solution was heated at 75° for 30 min and then allowed to cool. The solid which had deposited was collected by filtration, washed with 2N hydrochloric acid (50 ml) followed by ethanol (50 ml) and dried in vacuo to give the title compound as a powder (18.18 g), m.p. 280°-281°.

(iv) 2-(4-Hydrazinophenyl)-1,4,5,6-tetrahydropyrimidine dihydrochloride

A suspension of the product of Stage (iii) (17.8 g) in methanol (200 ml) containing concentrated hydrochloric acid (26 ml) was heated under reflux for 2 h. The solvent was removed by evaporation under reduced pressure and the residue was azeotropically dried using ethanol (2×50 ml). The residue was dissolved in refluxing methanol (200 ml) and propan-2-ol was periodically added to maintain the volume at 200 ml. When the temperature of the distillate had reached 80°, the suspension was cooled and the solid collected by filtration. Washing with propan-2-ol (50 ml) and drying in vacuo gave the title compound as prisms, (15.7 g), m.p. 283°-290°.

(v) 5-(1,4,5,6-Tetrahydro-2-pyrimidin-yl)-1H-indole-3-ethanamine dihydrochloride A mixture of the product of Stage (iv) (10.48 g) and 4-chlorobutanal (5.8 g, 73% pure) was stirred in methanol (320 ml) containing water (80 ml) for 15 min. After heating under reflux for 17 h, the solvent was evaporated under reduced pressure with periodic addition of ethanol to dry the material azeotropically. Ethanol (400 ml) containing water (10 ml) was added to the residue and the mixture was heated under reflux to dissolve the solid. The volume of the solution was reduced by 150 ml by distillation and then allowed to cool. Collection of the solid by filtration and washing with ethanol (50 ml) gave the title compound as a powder, (6.62 g), m.p.>300°.

Analysis Found: C, 53.34; H, 6.39; N, 17.77; $C_{14}H_{18}N_4.2HCl$ requires: C, 53.19; H, 6.41; N, 17.92%

The following examples illustrate pharmacetical formulations according to the invention, containing 3-[2-(dimethylamino)ethyl]-N-ethyl-1H-indole-5-carboximidamide dihydrochloride as the active ingredient. Other compounds of the invention may be formulated in a very similar manner.

TABLETS FOR ORAL ADMINISTRATION

DIRECT COMPRESSION

| | mg/tablet |
|---|---|
| Active ingredient | 2.4 |
| Calcium hydrogen phosphate B.P.* | 95.10 |
| Croscarmellose sodium USP | 2.00 |
| Magnesium stearate, B.P. | 0.50 |
| Compression weight | 100 mg |

*of a grade suitable for direct compression

The active ingredient is sieved before use. The calcium hydrogen phosphate, croscarmellose sodium and active ingredient are weighed into a clean polythene bag. The powders are mixed by vigorous shaking then the magnesium stearate is weighed and added to the mix which is blended further. The mix is then compressed using a Manesty F3 tablet machine fitted with 5.5 mm flat bevelled edge punches, into tablets with target compression weight of 100 mg.

Tablets may also be prepared by other conventional methods such as wet granulation.

Tablets of other strengths may be prepared by altering the ratio of active ingredient to lactose or the compression weight and using punches to suit.

The tablets may be film coated with suitable film forming materials, such as hydroxypropyl methylcellulose, using standard techniques. Alternatively the tablets may be sugar coated.

CAPSULES

|  | mg/capsule |
|---|---|
| Active ingredient | 2.4 |
| *Starch 1500 | 196.6 |
| Magnesium Stearate BP | 1.00 |
| Fill Weight | 200.00 |

*A form of directly compressible starch.

The active ingredient is sieved and blended with the excipients. The mix is filled into size No. 2 hard gelatin capsules using suitable machinery. Other doses may be prepared by altering the fill weight and if necessary changing the capsule size to suit.

SYRUP

|  | mg/5 ml dose |
|---|---|
| Active ingredient | 2.4 |
| Buffer | |
| Flavour | |
| Colour | |
| Preservative | as required |
| Thickening agent | |
| Sweetening agent | |
| Purified Water to | 5.00 ml |

The active ingredient, buffer, flavour, colour, preservative, thickening agent and sweetening agent are dissolved in some water, the solution is adjusted to volume and mixed. The syrup produced is clarified by filtration.

SUPPOSITORY FOR RECTAL ADMINISTRATION

| Active ingredient | 2.4 mg |
|---|---|
| *Witepsol H15 to | 1.0 g |

*A proprietary grade of Adeps Solidus Ph. Eur.

A suspension of the active ingredient in molten Witepsol is prepared and filled, using suitable machinery, into 1 g size suppository moulds.

INJECTION FOR INTRAVENOUS ADMINISTRATION

|  | mg/ml |
|---|---|
| Active ingredient | 0.6 mg |
| Sodium Chloride BP | as required |
| Water for Injection BP to | 1.0 ml |

Sodium chloride may be added to adjust the tonicity of the solution and the pH may be adjusted, using acid or alkali, to that of optimum stability and/or to facilitate solution of the active ingredient. Alternatively suitable buffer salts may be used.

The solution is prepared, clarified and filled into appropriate size ampoules sealed by fusion of the glass. The injection is sterilised by heating in an autoclave using one of the acceptable cycles. Alternatively the solution may be sterilised by filtration and filled into sterile ampoules under aseptic conditions. The solution may be packed under an inert atmosphere of nitrogen or other suitable gas.

We claim:

1. A compound of the formula (I)

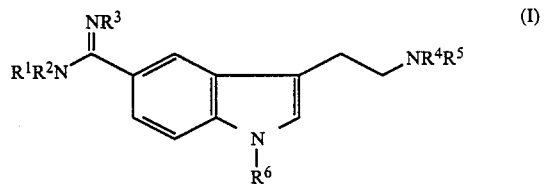

wherein one of $R^1$, $R^2$ and $R^3$ represents a hydrogen atom, a $C_{1-6}$ alkyl, $C_{3-6}$ alkenyl, hydroxy, $C_{1-4}$ alkoxy or a $C_{2-5}$ alkoxycarbonyl group, a phenyl or substituted phenyl group or a phen($C_{1-4}$)alkyl group, wherein the substituent on the phenyl or phenyl ($C_{1-4}$ alkyl) is $C_{1-4}$ alkyl, $C_{1-4}$ alkoxy, $C_{2-5}$ alkoxycarbonyl or a group of formula $R^7R^8NSO_2CH_2-$ or $R^7R^8NCOCH_2-$, where $R^7$ and $R^8$ each independently represent a hydrogen atom or a $C_{1-3}$ alkyl group; and the other two, which may be the same or different, each represents a hydrogen atom or a $C_{1-6}$ alkyl group, or $R^2$ and $R^3$ together form an alkylene chain $(-CH_2)_n-$ where n is 2 or 3, bridging the nitrogen atoms to which they are attached; $R^4$ and $R^5$, which may be the same or different each represents a hydrogen atom or a $C_{1-3}$ alkyl or propenyl group; $R^6$ represents a hydrogen atom or a $C_{1-3}$ alkyl group; and a physiologically acceptable salt or solvate thereof.

2. A compound according to claim 1, wherein in the formula (I), $R^1$ represents a $C_{1-3}$ alkyl group, and $R^2$ and $R^3$ each represents a hydrogen atom.

3. A compound according to claim 1, wherein in the formula (I), $R^1$ represents a substituted phenyl group and $R^2$ and $R^3$ each represents a hydrogen atom.

4. A compound according to claim 1, wherein in the formula (I), $R^2$ and $R^3$ together form a tetrahydropyrimidin-2-yl group.

5. A compound according to claim 1, wherein in the formula (I), $R^4$ and $R^5$, which may be the same or different, each represents a hydrogen atom or a methyl or ethyl group such that the total number of carbon atoms in $R^4$ and $R^5$ together does not exceed two.

6. 3-[2-(Dimethylamino)ethyl]-N-ethyl-1H-indole-5-carboximidamide and the physiologically acceptable salt and solvate thereof.

7. A compound according to claim 1, which is a physiologically acceptable acid addition salt selected from the hydrochloride, hydrobromide, sulphate, nitrate, phosphate, tartrate, citrate, fumarate, maleate, succinate and sulphonate.

8. A pharmaceutical composition which comprises an effective amount for use in the treatment of pain resulting from dilation of the carotid vascular bed of at least one compound of formula (I) as claimed in claim 1 or a physiologically acceptable salt or solvate thereof together with one or more pharmaceutically acceptable carriers or excipients.

9. A pharmaceutical composition according to claim 8, which comprises one or more other therapeutic agents selected from the group consisting of analgesics, anti-inflammatory agents and anti-nauseants.

* * * * *